US012791210B2

(12) United States Patent
Steen et al.

(10) Patent No.: US 12,791,210 B2
(45) Date of Patent: Nov. 10, 2026

(54) AIR TREATMENT SYSTEM USING PHOTOCATALYTIC OXIDATION (PCO)

(71) Applicant: Leidos Engineering, LLC, Walled Lake, MI (US)

(72) Inventors: William Ronald Steen, Clermont, FL (US); Paul Edward Floyd, Troy, MI (US); Jason Edward Jarrell, White Lake, MI (US)

(73) Assignee: Leidos Engineering, LLC, Walled Lake, MI (US)

( * ) Notice: Subject to any disclaimer, the term of this patent is extended or adjusted under 35 U.S.C. 154(b) by 1256 days.

(21) Appl. No.: 17/541,367

(22) Filed: Dec. 3, 2021

(65) Prior Publication Data

US 2023/0071631 A1 Mar. 9, 2023

Related U.S. Application Data

(60) Provisional application No. 63/242,140, filed on Sep. 9, 2021.

(51) Int. Cl.

| | |
|---|---|
| ***F24F 8/22*** | (2021.01) |
| ***A61L 9/20*** | (2006.01) |
| ***F24F 11/77*** | (2018.01) |
| ***F24F 110/20*** | (2018.01) |

(52) U.S. Cl.

CPC ................ *F24F 8/22* (2021.01); *A61L 9/205* (2013.01); *F24F 11/77* (2018.01); *A61L 2209/111* (2013.01); *A61L 2209/12* (2013.01); *A61L 2209/21* (2013.01); *F24F 2110/20* (2018.01)

(58) Field of Classification Search

CPC .............. F24F 8/22; F24F 11/77; A61L 9/205

See application file for complete search history.

(56) References Cited

U.S. PATENT DOCUMENTS 5,257,958 A * 11/1993 Jagers ................. F24D 19/1084 236/46 C
5,835,840 A * 11/1998 Goswami .................. A61L 9/20 422/186.3
5,933,702 A 8/1999 Goswami
6,358,374 B1 * 3/2002 Obee .................. B01D 53/0415 204/157.3
6,849,234 B2 * 2/2005 Lentz ...................... F24F 8/192 422/1
7,291,315 B2 * 11/2007 Obee ...................... B01D 53/96 422/186.3

(Continued)

FOREIGN PATENT DOCUMENTS

WO WO 2005/030387 A1 4/2005

OTHER PUBLICATIONS

International Search Report and Written Opinion issued Apr. 18, 2022, in PCT/US21/61791, 19 pages.

*Primary Examiner* — Brian W Cohen
*Assistant Examiner* — Nathanael Jason Downes
(74) *Attorney, Agent, or Firm* — McCarter & English, LLP

(57) ABSTRACT

Aspects of the present disclosure provide a system for abating a hydrocarbon compound (HCC) in air using photocatalytic oxidation (PCO). For example, the system can include an air handling unit (AHU), a sensor and a control panel. The AHU can be configured to abate HCC in air using PCO. The sensor can be configured to sense a level of the HCC in the air. The control panel can be configured to control the AHU based on the level of the HCC.

10 Claims, 3 Drawing Sheets

(56) References Cited

U.S. PATENT DOCUMENTS

| | | | | |
|---|---|---|---|---|
| 2003/0021720 | A1 | 1/2003 | Reisfeld et al. | |
| 2015/0033942 | A1 | 2/2015 | Zhang | |
| 2015/0114912 | A1 * | 4/2015 | Taghipour | C02F 1/725<br>210/748.14 |

* cited by examiner

AIR TREATMENT SYSTEM USING PHOTOCATALYTIC OXIDATION (PCO)

INCORPORATION BY REFERENCE

This present disclosure claims the benefit of U.S. Provisional Application No. 63/242,140, "AIR FILTRATION SYSTEM USING PHOTOCATALYTIC OXIDATION (PCO)" filed on Sep. 9, 2021, which is incorporated herein by reference in its entirety.

TECHNICAL FIELD

The present disclosure relates generally to abatement of hydrocarbon compounds (HCCs), such as peracetic acid (PAA), in air using photocatalytic oxidation (PCO).

BACKGROUND

Industries, such as the meat/poultry/food industry, pharmaceutical, medical, and others, can utilize bacterial abatement chemicals, such as peracetic acid (also known as peroxyacetic acid, or PAA), in their process water. The PAA outgasses from the process water into the plant air and is an irritant to employees' eyes, noses, and lungs. Conventionally, airborne PAA is diluted through the use of large volumes of outside air, and then exhausted to the outside.

SUMMARY

Aspects of the present disclosure provide a system for abating a hydrocarbon compound (HCC) in air using photocatalytic oxidation (PCO). For example, the system can include an air handling unit (AHU), a sensor and a control panel. The AHU can be configured to abate HCC in air using PCO. The sensor can be configured to sense a level of HCC in the air. The control panel can be configured to control the AHU based on the level of the HCC.

In an embodiment, the AHU can include one or more ultraviolet (UV) light systems that are configured to generate UV light and PCO media that is configured to act as a catalyst with the UV light to trigger oxidation of the HCC, and the control panel can be configured to control the UV light systems based on the level of the HCC. For example, the UV light systems can be configured to operate at different power states, and the control panel can be configured to control the UV light systems to operate at at least one of the power states based on the level of the HCC. As another example, the UV light systems can be configured to generate the UV light of different wavelengths, and the control panel can be configured to control the UV light systems to generate the UV light of at least one of the wavelengths based on the level of the HCC. In some other embodiments, the system can further include one or more panels of PCO media, wherein the PCO media can be contained in one or more panels of PCO media within the AHU allowing the air flow to be exposed to the catalytic process multiple times per pass. For example, at least one of the panels of PCO media can be disposed between two of the UV light systems with both sides of the panels of PCO media exposed to the UV light generated by the two UV light systems, respectively.

In an embodiment, the system can further include a fan system configured to adjust a flow rate of the air flowing through the AHU, wherein the control panel can be further configured to control the fan system to adjust the flow rate of the air flowing through the AHU based on the level of the HCC. For example, the fan system can include one or more variable speed fans, wherein the control panel can be further configured to control a fan speed of the variable speed fan based on the level of the HCC. As another example, the fan system can include a plurality of constant speed fans, wherein the control panel can be further configured to activate a number of the constant speed fans based on the level of the HCC.

In an embodiment, the system can further include an air conduit, wherein the AHU can be disposed within the air conduit. For example, the air conduit can have an inside air entrance, through which the air flows into the air conduit, and the sensor can be disposed within the air conduit between the inside air entrance and the AHU. As another example, the air conduit can have an HCC abated air exit, through which the air with the HCC abated by the AHU flows to a region outside of the air conduit, and the sensor can be disposed within the air conduit between the HCC abated air exit and the AHU. In some other embodiments, the system can further include a return air damper, wherein the air conduit can have an inside air entrance, through which the air flows into the air conduit, the return air damper can be disposed within the air conduit between the inside air entrance and the AHU and configured to regulate flow of the air passing through the inside air entrance into the air conduit, and the control panel can be further configured to control the return air damper to regulate the flow of the air based on the level of the HCC. In various embodiments, the system can further include a filter, wherein the air conduit can have an inside air entrance, through which the air flows into the air conduit, and the filter can be disposed within the air conduit between the inside air entrance and the AHU.

In an embodiment, the system can further include a humidity sensor and a humidifier or dehumidifier. The humidity sensor can be configured to sense a humidify level of the air. The humidifier or dehumidifier can be configured to regulate humidify of the air. The control panel can be further configured to control the humidifier or dehumidifier to regulate humidity of the air based on the humidify level sensed by the humidity sensor.

Aspects of the present disclosure further provide a method for abating an HCC in air using PCO. The method can include exposing PCO media to UV light to act as a catalyst for oxidation of HCC, and guiding air to flow through the PCO media. The method can further include sensing a level of HCC in the air, and adjusting a flow rate of the air flowing through the PCO media based on the level of the HCC. In an embodiment, the PCO media can be contained in a panel of PCO media, and both sides of the panel of PCO media can be exposed to the UV light.

In an embodiment, the method can further include adjusting the UV light based on the level of the HCC.

Aspects of the present disclosure further provide a non-transitory storage medium storing instructions that, when executed by a processing circuitry, cause the processing circuitry to control one or more UV light systems to generate and illuminate UV light to PCO media, a fan system to guide air to flow through the PCO media, a sensor to sense a level of HCC in the air, and the fan system to adjust a flow rate of the air flowing through the PCO media based on the level of the HCC.

In an embodiment, the instructions, when executed by the processing circuitry, can further cause the processing circuitry to control the UV light systems to generate and illuminate the UV light to the PCO media based on the level of the HCC.

This summary section does not specify every embodiment and/or incrementally novel aspect of the present disclosure or claimed invention. Instead, this summary only provides a preliminary discussion of different embodiments and corresponding points of novelty over conventional techniques. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION OF EMBODIMENTS

The system can draw air (e.g., peracetic acid (PAA) laden air) in a plant through an air handling unit (AHU) by a fan system and discharge clean air (e.g., PAA abated air) back to the plant. The PAA laden air in the plant will chemically interact with oxygen, which is triggered by photocatalytic oxidation via photocatalytic oxidation (PCO) media contained in one or more panels of PCO media with ultraviolet (UV) light in the AHU. The UV light can have the added benefit of killing bacteria and viruses. The PCO screens can contain PCO media of the same or different thickness and may be coated with various coating that act as a catalyst for photocatalytic oxidation of PAA or other HCCs.

The present disclosure can abate the PAA or other HCCs from the plant air, thereby reducing the amount of outside air required for dilution. By reducing the amount of PAA or other HCCs in the air, employee safety and comfort can be improved. The present disclosure can further reduce introduced humidity and reduce energy associated with heating and cooling outside air introduced to the plant for purposes of dilution. It should be noted, although not always explicitly stated, that PAA described herein is merely exemplary and that in some cases other HCCs may be used or PAA may refer to other HCCs.

The present disclosure can utilize PCO media that will, when exposed to UV light, act as a catalyst to oxidize PAA or other HCCs by reacting with oxygen in the air. This reaction will take place with PAA, as well as any other similar hydrocarbon compounds (HCC) in processing and manufacturing plant air. The PCO media triggered reaction converts the PAA or HCC to $CO_2$ and water.

The PCO media and UV light systems that generate the UV light can be installed in an AHU. A system will monitor PAA/HCC levels in the plant space and control the AHU fan speed, outside air damper, return air damper, and exhaust fan speed. The system will control the AHU fan speed, outside air damper, return air damper, and exhaust fan speed elements of the design to maximize the elimination of the PAA/HCC from the plant space.

The present disclosure can be installed in newly manufactured AHUs or retrofitted in existing AHUs.

Figure 1:
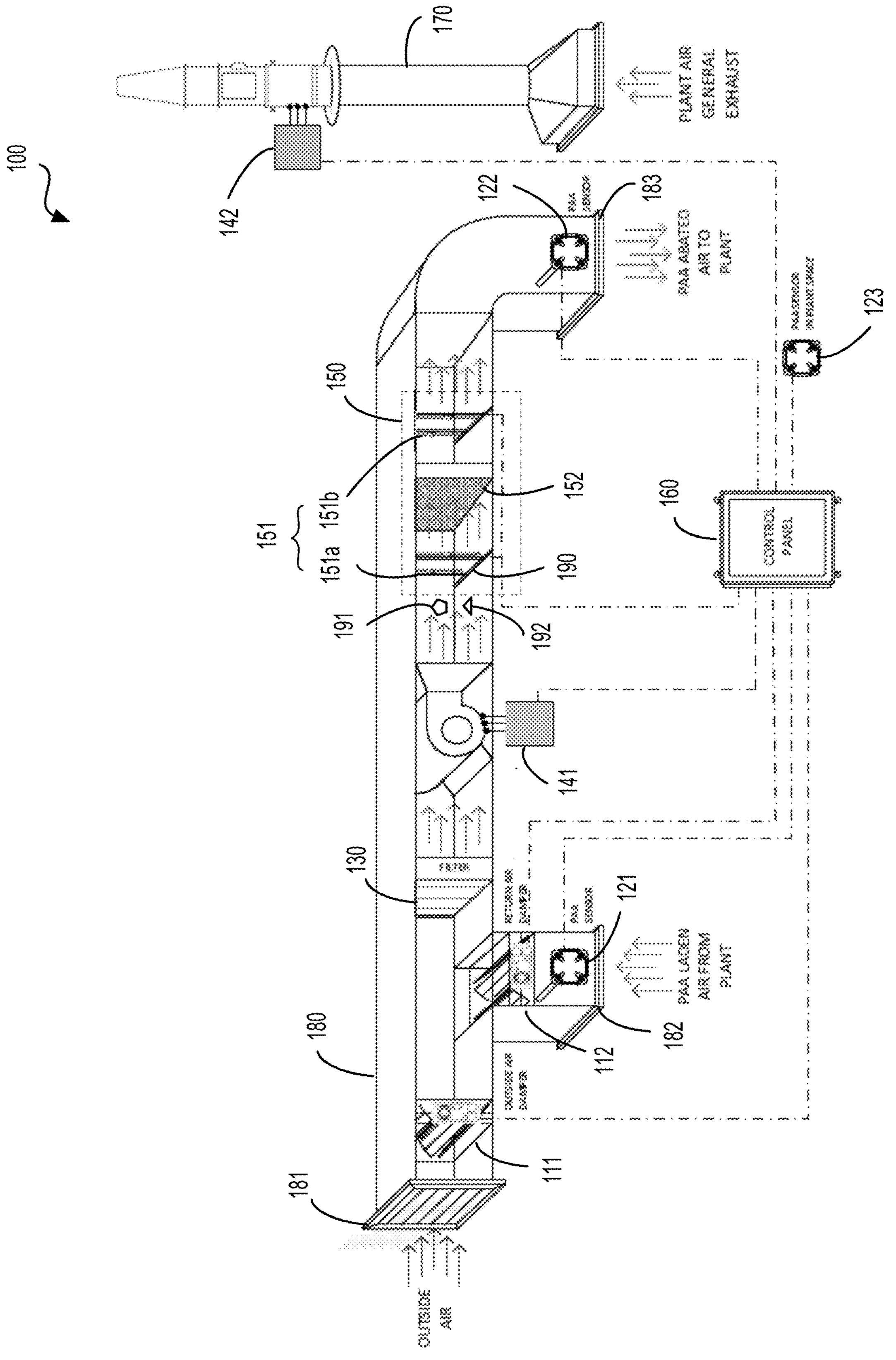
FIG. 1 shows an exemplary system for abating hydrocarbon compounds (HCC) in air using photocatalytic oxidation (PCO) in accordance with some embodiments of the present disclosure.

FIG. 1 shows an exemplary system 100 for abating HCC, such as PAA, in air using PCO in accordance with exemplary embodiments of the present disclosure. For example, the exemplary system 100 can be used in a variety of enclosed sites, such as meat/poultry/food processing plants, medical facilities, buildings, and the like. While not limited to, in some embodiments, the HCC can be PAA, which can be used as an antimicrobial for the meal/poultry/food. In an embodiment, the exemplary system 100 can be installed in an enclosed plant, and include a return air damper 112, a first HCC sensor (e.g., a first PAA sensor) 121, a second PAA sensor 122, a third PAA sensor 123, a filter 130, an inside fan system 141, an AHU 150, a control panel 160, and an air conduit 180. In another embodiment, the exemplary system 100 can further include an outside air damper 111, an exhaust system 170 and an outside fan system 142.

The air conduit 180 in the exemplary system 100 can have a rectangular cross-section, as shown in FIG. 1. However, persons having ordinary skills in the art will readily recognize that the air conduit 180 can have other cross-sectional shapes, such as a circular cross-section.

In an embodiment, the outside air damper 111 can be installed within the air conduit 180 near an outside air entrance 181 and stop or regulate the flow of air, e.g., outside air, outside the plant into the air conduit 180 in order to modify the PAA or other HCC level of the air in the plant. For example, the outside air damper 111 can be a valve or a plate. The outside air damper 111 is optional and can be excluded in some embodiments of the present disclosure.

In an embodiment, the return air damper 112 can be installed within the air conduit 180 near an inside air entrance 182 and stop or regulate the flow of air, e.g., PAA laden air, inside the plant through the inside air entrance 182 into the air conduit 180. For example, the return air damper 112 can be a valve or a plate.

The first PAA sensor 121 can be installed within the air conduit 180 near the return air damper 112 and sense a PAA level of the PAA laden air returning through the inside air entrance 182 into the air conduit 180. The second PAA sensor 122 can be installed within the air conduit 180 near a PAA abated air exit (or an HCC abated air exit) 183 and sense a PAA level of the PAA abated air output from the AHU 150. The third PAA sensor 123 can be installed in a certain location of the plant to sense a PAA level of the PAA laden air there.

The filter 130 can be a device or structure that filters out particles, for example, in the outside air flowing from the outside air damper 111 and the PAA laden air flowing from the return air damper 112. In an embodiment, the filter 130 can include an air filter material. For example, the filter 130 can include a net-like filter made of resin or the like. As another example, the filter 130 can include a sponge-like filter. Therefore, the filter 130 can have small air resistance, and the pressure loss at the outside air entrance 181 and the inside air entrance 182 can be reduced.

The inside fan system 141 can include an inside variable speed fan, which can increase or decrease the air speed in the air conduit 180. The outside fan system 142 can include an outside variable speed fan, which can increase or decrease the air speed in the exhaust system 170, which can thus be referred to as a variable exhaust. In some other embodiments, each of the inside fan system 141 and the outside fan system 142 can include multiple constant speed fans, and can increase or decrease the air speed in the air conduit 180 and the exhaust system 170 by activating more or fewer constant speed fans. For example, the inside fan system 141 and the outside fan system 142 can include propeller fans and/or sirocco fans. As another example, the inside fan system 141 and the outside fan system 142 can include axial fans and/or centrifugal fans.

The AHU 150 can be disposed within the air conduit 180, and abate, via oxidation, the PAA contained in the PAA laden air using oxygen in the air triggered by the photocatalytic oxidation (PCO) of the PCO media upon exposition and illumination with ultraviolet (UV) light. For example, the AHU 150 can include one or more UV light systems 151 and one or more panels of PCO media 152, each of the panels of PCO media 152 containing the PCO media. The UV light systems 151 can generate UV light, and the PCO media contained in the panels of PCO media 152 can be exposed to the UV light and act as a catalyst by the UV light to trigger the oxidation of the PAA contained in the PAA laden air.

The UV light systems 151 can include one or more bars (or baffles) 151*a* that are installed in tracks 190 and UV light emitting devices 151*b* that are mounted onto the bars 151*a*. The tracks 190 (and the UV light systems 151 as well) can be disposed at spaced locations within the air conduit 180. In an embodiment, the UV light emitting devices 151*b* can emit UV light (having wavelengths between 100 to 400 nm), such as UVA light (wavelengths of 400 to 315 nm), UVB light (wavelengths of 315 to 280 nm) and UVC light (wavelengths of 280 to 200 nm). For example, the UV light emitting devices 151*b* can be germicidal lamps, which can emit UVC light, which can disrupt DNA base pairing and lead to the inactivation of bacteria, viruses and protozoa. As another example, the UV light emitting devices 151*b* can include low-pressure mercury lamps, high-pressure mercury lamps, excimer lamps, and/or light emitting diodes (LEDs).

The panels of PCO media 152 can be disposed alternatively with the UV light systems 151 within the air conduit 180. For example, the AHU 150 can include two UV light systems 151 and one panel of PCO media with both sides facing and exposed to the two UV light systems 151, respectively, as shown in FIG. 1. However, the numbers of the panels of PCO media 152 and the UV light systems 151 are representative. In an embodiment, the number of the panels of PCO media 152 can be less than that of the UV light systems 151 by one so that each side of each of the panels of PCO media 152 can be exposed to the UV light emitted by one of the UV light systems 151. In some other embodiments, more or fewer UV light systems 151 and panels of PCO media 152 can be provided. For example, the AHU 150 can include more than one panel of PCO media 152, e.g., three panels of PCO media, and one or more than two UV light systems 151, e.g., four UV light systems, to increase the ability to remove the PAA contained in the PAA laden air.

Maximizing the exposure of the panels of PCO media 152 to the UV light emitted by the UV light systems 151 can maximize the effectiveness of the panels of PCO media 152. In an embodiment, the UV light emitting devices (e.g., UV LEDs) 151*b* can operate at a high power state, thus generating a large luminous flux of UV light to activate the PCO media contained in the panels of PCO media 152. In another embodiment, neighboring panels of PCO media and UV light system 151 (and the track 190 on which the UV light system 151 is mounted) can be spaced at a distance such that the illumination spots of the UV LEDs 151*b* of the UV light system 151 can just overlap, thus fully illuminating the entire facing surface of the panels of PCO media 152. For example, the UV LEDs 151*b* mounted on the bar (or baffle) 151*a* can be arranged in an array. As another example, the UV LEDs 151*b* mounted on the bar (or baffle) 151*a* can be arranged in a honeycomb manner.

Upon the exposure of the PCO media contained in the panels of PCO media 152 to the UV light emitted by the UV light systems 151, electrons can be excited from the valence band to the conduction band, which results in the generation of charge carriers, i.e., electron-hole pairs ($e^-$-$h^+$). These generated charge carriers can subsequently react with water molecules in a vapor state in the air absorbed onto the surface of the PCO media to produce reactive species such as hydroxyl radicals (*OH). These free radicals (regarded as the main oxidants in PCO), in turn, can oxidize the PAA/HCC into $CO_2$ and $H_2O$ primarily and some light by-products.

In an embodiment, the PCO media can include $TiO_2$ (also called titania), ZnO, $ZrO_2$, $WO_3$ and/or $SnO_2$. $TiO_2$ is widely considered as the most efficient and promising PCO media in the art. The PCO media, e.g., $TiO_2$, can be prepared and coated onto the panels of PCO media 152. For example, a calculated amount of $TiO_2$ can be added to deionized water, and the solution can be stirred to obtain a homogeneous $TiO_2$ suspension, which can then be coated on the panels of PCO media (which can be made from Ni foam, for example). The panels of PCO media with the $TiO_2$ suspension coated thereonto can undergo a drying process to remove water. $TiO_2$ can be synthesized in three crystal phases: anatase, rutile and brookite. As another example, the panels of PCO media 152 can include nonwoven fabric, non-cured binder in which the PCO media is dispersed can be impregnated into the nonwoven fabric, and then the PCO media can be immobilized on the nonwoven fabric by solidifying the binder. The binder can be inorganic binder (including silane compounds, for example) or organic binder (including acrylic compounds, for example).

The exhaust system (or variable exhaust) 170 can exhaust the air (or the PAA laden air and the PAA abated air) in the plant to a region outside of the plant.

The control panel 160 can control the outside air damper 111, the return air damper 112, the inside fan system 141, the outside fan system 142 and the AHU 150 (or the UV light systems 151) based on the PAA level of the first to third PAA sensors 121 to 123. For example, when the PAA level of the PAA laden air sensed by the first PAA sensor 121 and/or the third PAA sensor 123 and/or the PAA level of the PAA abated air sensed by the second PAA sensor 122 is greater than a first PAA level threshold, the control panel 160 can increase the fan speed of the inside fan system 141 and/or the outside fan system 142 (which can include a variable speed fan) or activate more constant speed fans in the inside fan system 141 and/or outside fan system 142, regulate the outside air damper 111 and/or the return air damper 112, and/or control the UV light systems 151 to generate UVC light or to operate at a high power state. As another example, when the PAA level of the PAA laden air sensed by the first PAA sensor 121 and/or the third PAA sensor 123 and/or the PAA level of the PAA abated air sensed by the second PAA sensor 122 is less than a second PAA level threshold, which can be less than the first PAA level threshold, the control panel 160 can decrease the fan speed of the inside fan system 141 and/or the outside fan system 142 (which can include a variable speed fan) or activate fewer constant speed fans in the inside fan system 141 and/or the outside fan system 142, regulate or even stop the outside air damper 111 and/or the return air damper 112, and/or control the UV light systems 151 to generate UVA light, to operate at a low power state or even to be turned off.

Optionally, the exemplary system 100 can further include other components based on demands. For example, the exemplary system 100 can further include a humidity sensor 191 and a humidifier or dehumidifier 192. In an embodiment, the humidity sensor 191 and the humidifier or dehumidifier 192 can be disposed within the air conduit 180 near the AHU 150, and the control panel 160 can further control the humidifier or dehumidifier 192 to regulate the humidity of the air within the air conduit 180 based on the humidity level sensed by the humidity sensor 191. For example, when the humidity sensor 191 senses that the humidity of the air within the air conduit 180 is greater than a humidity level threshold, the control panel 160 can control the humidifier or dehumidifier 192 to reduce the humidity level of the air, as the presence of too much the water vapor in the air may significantly affect the PCO reactions.

The exemplary system 100 can further include some other components, such as burners, hot water or steam coils and chilled water or refrigerant coils, which can heat, pre-heat, re-heat, cool or pre-cool the air in the air conduit 180.

Figure 2:
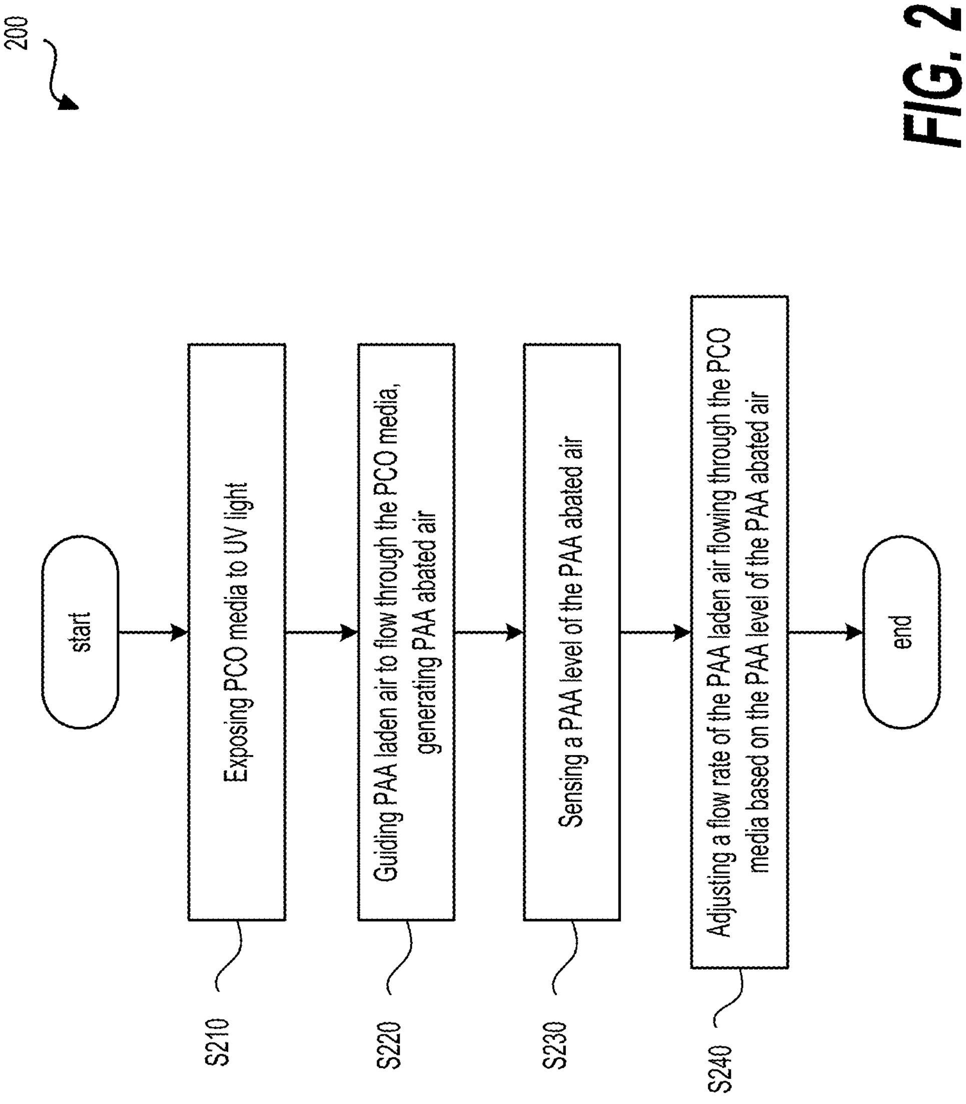
FIG. 2 is a flow chart illustrating an exemplary method for abating HCC in air using PCO in accordance with some embodiments of the present disclosure.

FIG. 2 is a flow chart illustrating an exemplary method 200 for abating HCC (e.g., PAA) in air using PCO in accordance with some embodiments of the present disclosure. For example, the exemplary method 200 can be performed by the exemplary system 100. In an embodiment, some of the steps of the exemplary method 200 shown can be performed concurrently or in a different order than shown, can be substituted by other method steps, or can be omitted. Additional method steps can also be performed as desired.

At step S210, PCO media, such as $TiO_2$, can be provided and exposed to UV light to cause the PCO media to act as a catalyst for the oxidation of PAA. For example, the panels of PCO media 152 containing the PCO media thereon can be exposed to the UV light emitted by the UV light systems 151. Upon the exposure of the PCO media to the UV light, electrons can be excited from the valence band to the conduction band, which results in the generation of charge carriers. These charge carriers can subsequently react with water molecules in a vapor state in the air to produce hydroxyl radicals (*OH). In an embodiment, both sides of at least one of the panels of PCO media 152 can be exposed to the UV light.

At step S220, PAA laden air can be guided to flow through the PCO media, thus generating PAA abated air. For example, the inside fan system 141 can guide the PAA laden air to flow from the inside air entrance 182 through the PCO media contained on the panels of PCO media 152. The free hydroxyl radicals (*OH) generated at step S210, in turn, can oxidize the PAA in the PAA laden air into $CO_2$ and $H_2O$.

At step S230, a PAA level of the PAA abated air can be sensed. For example, the PAA level of the PAA abated air can be sensed by the second PAA sensor 122. Alternatively or additionally, another PAA level of the PAA laden air can also be sensed. For example, the another PAA level of the PAA laden air can be sensed by the first PAA sensor 121 and/or the third PAA sensor 123.

At step S240, a flow rate of the PAA laden air flowing through the PCO media at step S220 can be adjusted based on the PAA level of the PAA abated air and/or the another PAA level of the PAA laden air. For example, when the sensed PAA level of the PAA abated air is greater than the first PAA level threshold, the control panel 160 can control the inside fan system 141 and/or the outside fan system 142, which can include variable speed fans, to increase the flow rate of the PAA laden air by increase the air speed in the air conduit 180. As another example, when the sensed PAA level of the PAA abated air is less than the second PAA level threshold, the control panel 160 can activate fewer constant speed fans in the inside fan system 141 and/or the outside fan system 142 to decrease the flow rate.

Alternatively or additionally, at step S240 the intensity and/or wavelength of the UV light can also be adjusted based on the PAA level of the PAA abated air and/or the another PAA level of the PAA laden air. For example, when the sensed PAA level of the PAA abated air is greater than the first PAA level threshold, the control panel 160 can control the UV light systems 151 to operate at a high power state or to generate UVC light. As another example, when the sensed PAA level of the PAA abated air is less than the second PAA level threshold, the control panel 160 can control the UV light systems 151 to operate at a low power state or to generate UVA light.

Figure 3:
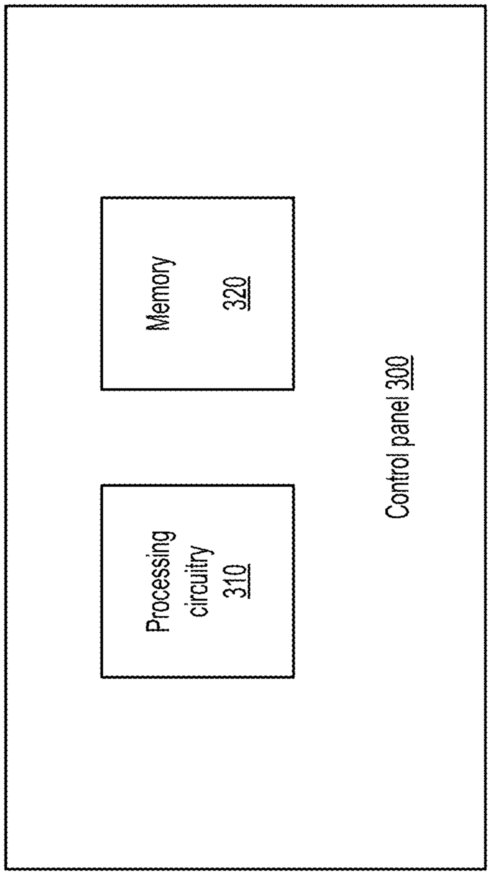
FIG. 3 is functioning block diagram of an exemplary control panel in accordance with some embodiments of the present disclosure.

FIG. 3 is a functioning block diagram of an exemplary control panel 300 in accordance with some embodiments of the present disclosure. In an embodiment, the exemplary control panel 300 can be configured to control the outside air damper 111, the return air damper 112, the inside fan system 141, the outside fan system 142 and the AHU 150 (or the UV light systems 151) based on the PAA level of the first to third PAA sensors 121 to 123 of the exemplary system 100. For example, the exemplary control panel 300 can include the control panel 160. In an embodiment, the exemplary control panel 300 can include processing circuitry 310 and a memory 320.

The memory 320 (e.g., a non-transitory computer-readable storage medium) can be configured to store instructions, programs, codes, and data (e.g., the first and second PAA level thresholds). For example, the memory 320 can include a volatile memory and/or a non-volatile memory. The non-volatile memory can be a read-only memory (ROM), a programmable read-only memory (PROM), an erasable PROM (EPROM), an electrically EPROM (EEPROM) or a flash memory. The volatile memory can be a random access memory (RAM), which is used as an external cache. By way of exemplary but not restrictive description, many forms of the RAM are available, such as a static RAM (SRAM), a dynamic RAM (DRAM), and a synchronous DRAM (SDRAM), a double data rate SDRAM (DDR SDRAM), an enhanced SDRAM (ESDRAM), a synch link DRAM (SLDRAM) and a direct rambus RAM (DR RAM).

The processing circuitry 310 can execute the instructions, programs or codes to perform the exemplary method 200 and/or cause the outside air damper 111, the return air damper 112, the inside fan system 141, the outside fan system 142 and the AHU 150 (or the UV light systems 151) to operate based on the PAA level sensed by the first to third PAA sensors 121 to 123. In an embodiment, instructions stored in the non-transitory storage medium 320, when executed by the processing circuitry 310, can cause the processing circuitry 310 to control one or more UV light systems (e.g., the UV light systems 151) to generate and illuminate UV light to PCO media (e.g., the PCO media contained in the panels of PCO media 152), a fan system (e.g., the inside fan system 141) to guide air to flow through the PCO media, a sensor (e.g., the first to third PAA sensors 121 to 123) to sense a level of HCC (e.g., PAA) in the air, and the fan system to adjust a flow rate of the air flowing through the PCO media based on the level of the HCC. In another embodiment, the instructions, when executed by the processing circuitry 310, can further cause the processing circuitry to control the UV light systems to generate and illuminate the UV light to the PCO media based on the level of the HCC.

For example, the processing circuitry 310 can be a digital signal processor (DSP), an application specific integrated circuit (ASIC), programmable logic devices (PLDs), field programmable gate arrays (FPGAs), digitally enhanced circuits, or comparable device or a combination thereof. In some other embodiments, the processing circuitry 310 can be a central processing unit (CPU) configured to execute program instructions to perform various functions and processes described herein.

The methods and functions described herein can be implemented as a computer program which, when executed by one or more processors, can cause the one or more processors to perform the respective processes and functions. The computer program may be stored or distributed on a suitable medium, such as an optical storage medium or a solid-state medium supplied together with, or as part of, other hardware. The computer program may also be distributed in other forms, such as via the Internet or other wired or wireless telecommunication systems. For example, the computer program can be obtained and loaded into an apparatus, including obtaining the computer program through physical medium or distributed system, including, for example, from a server connected to the Internet.

The computer program may be accessible from a computer-readable medium providing program instructions for use by or in connection with a computer or any instruction execution system. The computer readable medium may include any apparatus that stores, communicates, propagates, or transports the computer program for use by or in connection with an instruction execution system, apparatus, or device. The computer-readable medium can be magnetic, optical, electronic, electromagnetic, infrared, or semiconductor system (or apparatus or device) or a propagation medium. The computer-readable medium may include a computer-readable non-transitory storage medium such as a semiconductor or solid state memory, magnetic tape, a removable computer diskette, a random access memory (RAM), a read-only memory (ROM), a magnetic disk and an optical disk, and the like. The computer-readable non-transitory storage medium can include all types of computer readable medium, including magnetic storage medium, optical storage medium, flash medium, and solid state storage medium.

While aspects of the present disclosure have been described in conjunction with the specific embodiments thereof that are proposed as examples, alternatives, modifications, and variations to the examples may be made. Accordingly, embodiments as set forth herein are intended to be illustrative and not limiting. There are changes that may be made without departing from the scope of the claims set forth below.

What is claimed is:

1. A system for abating a hydrocarbon compound (HCC) in air using photocatalytic oxidation (PCO), comprising:
- an air entrance to receive HCC laden air, the air entrance having a damper to regulate flow of the HCC laden air into the system,
- a first HCC sensor downstream of the air entrance to sense a laden HCC level of the HCC laden air;
- a fan system to increase or decrease air speed through the system;
- an air handling unit (AHU) downstream of the first HCC sensor, the AHU configured to abate HCC in air using PCO, the AHU comprising:
  - a panel of PCO media, the panel configured to react with UVA light and with UVC light to trigger oxidation of the HCC and to abate the HCC in the HCC laden air,
  - a first ultraviolet (UV) light system upstream of the panel, the first UV light system configured to expose a first side of the panel with the UVA light or with the UVC light;
  - a second UV light system downstream of the panel, the second UV light system configured to expose a second side of the panel with the UVA light or with the UVC light, wherein the first and second UV light systems are configured to operate at a plurality of different power states including at least one of a high power state and a low power state;
  - an abated air exit downstream of the AHU to provide an egress to HCC abated air; and
  - a second HCC sensor associated with the abated air exit to sense an abated HCC level of the HCC abated air; and
- a control panel configured to control any of the damper, the inside fan system, or the AHU based on either of the laden HCC level or the abated HCC level, the control panel further configured to operate the first and second UV light systems to generate the UVA light and the UVC light in one or more of the plurality of different power states based on either of the sensed laden HCC level or the sensed abated HCC level.

2. The system of claim 1, wherein the control panel is further configured to generate the UVC light at the high power state and to generate the UVA light at the low power state.

3. The system of claim 1, wherein the inside fan system includes a variable speed fan, wherein the control panel is further configured to control a fan speed of the variable speed fan based on either of the laden HCC level or the abated HCC level.

4. The system of claim 1, wherein the fan system includes a plurality of constant speed fans, wherein the control panel is further configured to activate a number of the constant speed fans based on either of the laden HCC level or the abated HCC level.

5. The system of claim 1, further comprising:
- an outside air entrance to receive outside air, the outside air entrance having an outside air damper;
- the control panel further configured to control the outside air damper to regulate dilution of the HCC laden air with the outside air.

6. The system of claim 1, further comprising:
- a humidity sensor configured to sense a humidity level of the HCC laden air, the humidity sensor disposed upstream of the AHU; and
- a humidifier or dehumidifier configured to regulate the humidity of the HCC laden air, the humidifier or the dehumidifier disposed upstream of the AHU;
- the control panel is further configured to control the humidifier or the dehumidifier to regulate the humidity of the HCC laden air based on the humidity level sensed by the humidity sensor.

7. A method for abating a hydrocarbon compound (HCC) in air using photocatalytic oxidation (PCO), comprising:
- exposing, using an air handling unit (AHU) operatively coupled to a fan system, a panel of PCO media to first and second ultraviolet (UV) light systems to act as a catalyst for oxidation of the HCC to abate the HCC in HCC laden air, the first UV light system located upstream of the panel and configured to expose a first side of the panel with UVA light or with UVC light, and the second UV light system located downstream of the panel and configured to expose a second side of the panel with the UVA light or with the UVC light;

guiding the HCC laden air to flow through the PCO media by:

receiving, upstream of the AHU, at an air entrance having a damper, HCC laden air and regulating, using the damper, flow of the HCC laden air, receiving the HCC laden air from the air entrance and increasing or decreasing air speed downstream thereof using the fan system, and providing, at an abated air exit downstream of the AHU, an egress to HCC abated air, sensing, using a first HCC sensor downstream of the air entrance, a laden HCC level of the HCC in the HCC laden air, and sensing, using a second HCC sensor associated with the abated air exit, an abated HCC level of HCC abated air; and adjusting, using a control panel, any of the damper, the fan system, or the AHU based on either of the laden HCC level or the abated HCC level, wherein the first and second UV light systems are configured to operate at a plurality of different power states including at least one of a high power state and a low power state, and the adjusting comprises causing the first and second UV light systems to generate the UVA light and the UVC light in one or more of the plurality of different power states based on either of the sensed laden HCC level or the sensed abated HCC level.

8. The system of claim 1, wherein the HCC comprises peracetic acid (PAA), and the PCO media are configured to react with at least one of the UVA light or the UVC light to trigger oxidation of the PAA.

9. The system of claim 1, the control panel being further configured to:

operate at the high power state of the plurality of different power states when either of the laden HCC level or the abated HCC level is greater than a first threshold; and operate at the low power state of the plurality of different power states when either of the laden HCC level or the abated HCC level is less than a second threshold;

the second threshold being less than the first threshold.

10. The system of claim 1, further comprising a heating component or a cooling component to heat, pre-heat, re-heat, cool, or pre-cool the air.

* * * * *